(12) United States Patent
Muller-Fiedler et al.

(10) Patent No.: US 6,605,804 B1
(45) Date of Patent: Aug. 12, 2003

(54) OPTICAL SENSOR

(75) Inventors: Roland Muller-Fiedler, Leonberg (DE); Helmut Sautter, Ditzingen (DE); Joachim Schneider, Nattheim (DE); Anton Pfefferseder, Sauerlach-Arget (DE); Winfried Bernhard, Gerlingen (DE); Andre Mueller, Gerlingen (DE); Andreas Hensel, Vaihingen (DE); Ulrich Oppelt, Zorneding (DE); Lutz Mueller, Gerlingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/623,717

(22) PCT Filed: Sep. 24, 1998

(86) PCT No.: PCT/DE98/02848
§ 371 (c)(1),
(2), (4) Date: Jan. 23, 2001

(87) PCT Pub. No.: WO99/45369
PCT Pub. Date: Sep. 10, 1999

(30) Foreign Application Priority Data

| Mar. 7, 1998 | (DE) | 198 09 895 |
| Jun. 25, 1998 | (DE) | 198 28 343 |

(51) Int. Cl.$^7$ .................. G01J 3/50; G01J 1/48
(52) U.S. Cl. ............... 250/227.23; 250/226; 356/402; 422/86; 436/167
(58) Field of Search .............. 250/226, 227.23, 250/227.11; 356/402, 412, 437, 135, 136; 422/86, 87; 436/167

(56) References Cited

U.S. PATENT DOCUMENTS

| 4,352,779 A | * | 10/1982 | Parks | 422/52 |
| 4,634,879 A | * | 1/1987 | Penney | 250/561 |
| 4,657,744 A | * | 4/1987 | Howard | 422/52 |
| 4,677,078 A | | 6/1987 | Minten et al. | |
| 5,681,532 A | * | 10/1997 | Kane et al. | 422/82.06 |
| 5,728,422 A | * | 3/1998 | Kane et al. | 427/163.2 |
| 6,230,545 B1 | * | 5/2001 | Adolph et al. | 73/31.05 |
| 6,254,829 B1 | * | 7/2001 | Hartmann et al. | 422/82.06 |

FOREIGN PATENT DOCUMENTS

| EP | 0 120 231 | 10/1984 |
| EP | 0 193 037 | 9/1986 |
| EP | 0 352 631 | 1/1990 |
| EP | 0 434 893 | 7/1991 |

* cited by examiner

*Primary Examiner*—Stephone B. Allen
(74) *Attorney, Agent, or Firm*—Kenyon & Kenyon

(57) ABSTRACT

An optical sensor is provided for determining a physical and/or chemical parameter of a sample, having at least one optical transmitter and at least one optical receiver, and having a sensitive element which is arranged in a beam path between the transmitter and the receiver and is exposable to the sample, and which changes its absorption and/or its refractive index for electromagnetic radiation of a specific wavelength in response to a change in parameters of the sample, in particular, a gas-sensitive element, and possibly having an evaluation unit arranged downstream of the receiver. The transmitter and the receiver can be coupled to the sensitive element via at least one optical waveguide.

Provision is made for the transmitter (12) and for the receiver (14) to be coupled to the sensitive element via at least one optical waveguide (26, 28).

26 Claims, 4 Drawing Sheets

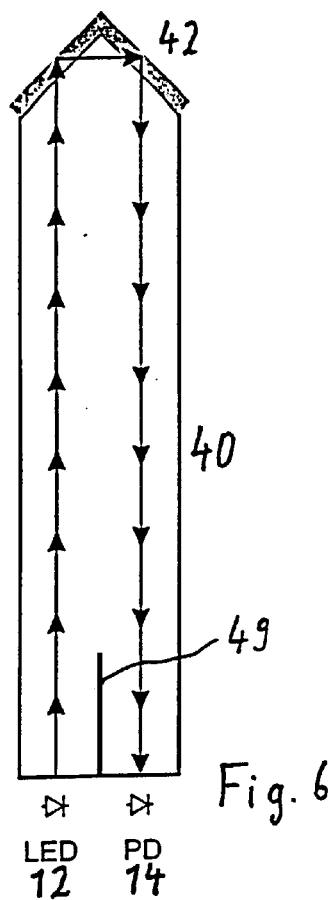
Fig. 6
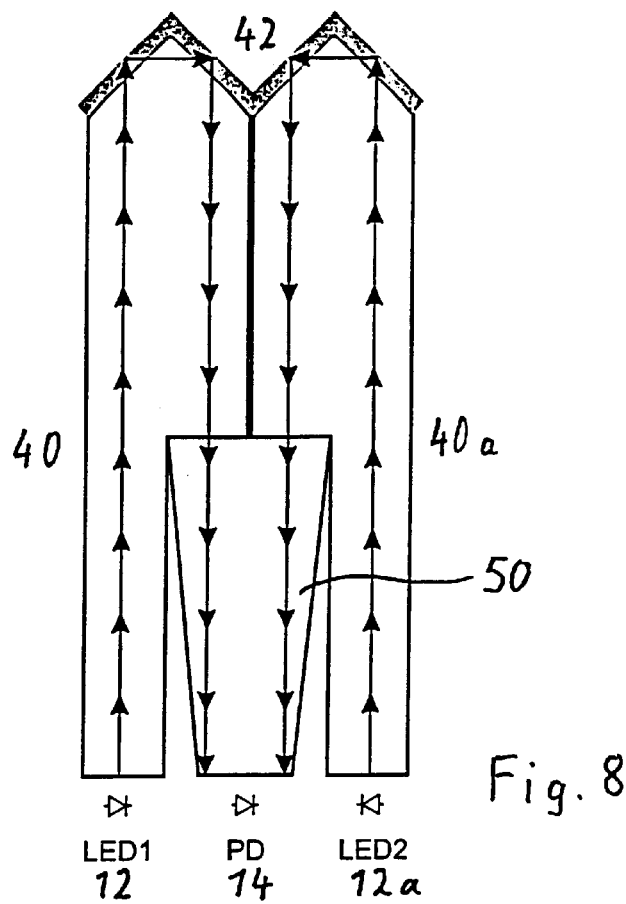
Fig. 8
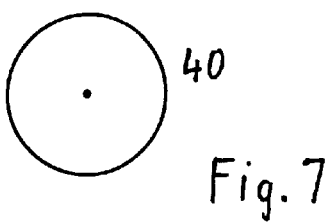
Fig. 7
Fig. 9
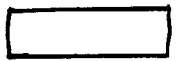
Fig. 13
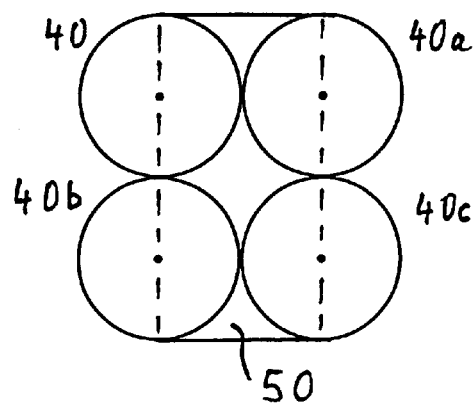
Fig. 10

OPTICAL SENSOR

BACKGROUND INFORMATION

There is a plurality of fields of application for sensors. These include the use of gas sensors for early fire detection. Thus, prior German patent application 197 41 335.8 describes optical gas sensors which are based on an interaction of specific gases with a semitranslucent layer, an absorption factor of light of a specific wavelength being dependent on the gas concentration. Disadvantageous in the known optical gas sensors are the relatively complex and voluminous measurement set-ups since, apart from an optical transmitter and an optical receiver, it is required to arrange a gas-sensitive layer within a beam path between these two components. In particular, measurements where the intention is for gas concentrations to be measured at points which are spatially distant from the optical components and which are, for example heavily thermally stressed, are possible only with difficulty.

SUMMARY OF THE INVENTION

The optical sensor according to the present invention offers the advantage that very compact and inexpensive, integrated components are picturable because of the spatial separability of the at least one optical transmitter and the at least one optical receiver and because of a sensitive layer which interacts with a sample, for example, a gas or a gas mixture, and which changes the transmission of light of a specific wavelength. If an integrated module preferably composed of an optical transmitter and of an optical receiver, is coupled via optical waveguides to the sensitive layer, which can be installed at any distant location, these units can completely be spatially separated from one another and, consequently, the gas-sensitive layer can be positioned at locations where, due to the spatial conditions or because of the thermal or mechanical conditions, no sensitive optical and/or electronic components can be installed.

By using, as the sensitive element, a gas-sensitive layer or membrane, also designated as optode, which is substantially permeable to electromagnetic radiation, and which changes its absorption properties and/or its refractive index for electromagnetic radiation in response to a contact with a gas or a gas mixture, very compact and miniaturizable gas sensors can be manufactured in simple manner. Understood by an optode in connection with the present invention, are, in particular, polymer layers which, due to indicator substances intercalated therein, exhibit a dependency of the light transmission on the concentration of a specific gas in the atmosphere surrounding the optode. Optodes which are used according to the present invention respond to the concentration of a specific gas in a selective and reversible manner. By measuring the absorption properties of the indicator substance which is present in the gas-sensitive layer or membrane, and which is exposed to and interacts with the gas, it is possible for very low gas concentrations to be measured and detected using relatively simple optical devices. The indicator substance present in the gas-sensitive layer and preferably intercalated in a polymer matrix, preferably responds only to a specific gas so that, using different indicator substances, sensors acting in a gas-specific manner are picturable, respectively.

In an advantageous embodiment of the optical sensor, a gas-sensitive layer having an applied or integrated indicator substance is interpositioned in the beam path of at least one source for electromagnetic radiation, preferably an optical transmitter, and of at least one detector for electromagnetic radiation, preferably an optical receiver, the gas-sensitive layer changing the transmission or absorption properties for the electromagnetic radiation depending on the physical and/or chemical interaction with a specific gas. The gas-sensitive layer is coupled to the transmitter and to the receiver via at least one optical waveguide. The source for electromagnetic radiation can be, for example, a light-emitting diode as optical transmitter, the light-emitting diode emitting light having a suitable wavelength. Accordingly, a photodiode is possible as optical receiver having a frequency range matched to the emitted wavelength of the light-emitting diode. Such a design can be implemented in simple manner with very inexpensive component parts. The gas-sensitive layer with the indicator substance contained therein or applied thereto, which is arranged in the beam path between optical transmitter and optical receiver is quantitatively calibrated at specific light wavelengths, preferably in a manner corresponding to its absorption properties, so that different gases can be detected using different light wavelengths with differently responding indicator substances.

Furthermore, it is advantageous to combine a plurality of optical transmitters with a plurality of gas-sensitive layers capable of detecting different gases, respectively, so that different gases can be detected using a single device. It can also be advantageous for the at least one optical transmitter and/or the at least one optical receiver to be directly provided or coated with a gas-sensitive layer. In this manner, a plurality of optical receivers provided with layers which are sensitive to different gases, respectively, can be irradiated by a plurality of optical transmitters or also by only one optical transmitter which, in this case, covers the entire required wavelength range.

The beam path between optical transmitter and optical receiver, including the intermediate gas-sensitive layer, can be extended in advantageous manner by using optical waveguides as optical coupling elements. In this manner, at least two optical transmitters and receivers positioned at different locations can be optically coupled with a gas-sensitive layer. Also possible is a spatial assembly of optical transmitter and optical receiver at the same location as well as an optical coupling over a very large distance using two optical waveguides led in parallel. The optical waveguides can be diverted or bent at their coupling point to the gas-sensitive layer in such a manner that their end faces, at which the light emerges or enters perpendicularly, are located in a parallel manner opposite each other, the gas-sensitive layer lying in between in the optical axis.

In an advantageous embodiment, the ends of the optical waveguides to be optically coupled to the gas-sensitive layer are chamfered at their sides facing away from the gas-sensitive layer in such a manner that the light beam guided in the optical waveguides is reflected toward the air at these interfaces (boundary surfaces). If the ends of the optical waveguides are chamfered to 45°, the light is reflected by 90° correspondingly, and exits the respective optical waveguide perpendicularly to the longitudinal direction thereof. If one end of the optical waveguide or both ends are coated with a gas-sensitive layer in a manner that the gas-sensitive layer is located in the beam path of a light beam running between the optical waveguides in the medium to be examined, it is possible for an optical detecting device for gases which has an extremely compact and simple design to be implemented at an arbitrary mounting location.

In a further advantageous embodiment, provision is made to use only one optical waveguide which, due to its special design including a conical peak and a gas-sensitive layer applied thereto, allows gases to be effectively detected also at locations which can be very far away from optical transmitter and receiver. In this context, at one end of the optical waveguide, the optical transmitters and receivers are arranged in such a manner that the light beam emanating from the optical transmitter runs parallel to the light beam guided toward the optical receiver within the optical waveguide. Therefore, the optical waveguide used in this connection expediently has a diameter which allows optical transmitters and receivers which can be considerably miniaturized to be arranged side by side. At the other end, the optical waveguide expediently has a conical peak which is partially or completely covered with a gas-sensitive layer. In this context, the cone angle should approximately be 90°, to achieve a desired twice repeated deflection of the light by 90°, i.e., by a total of 180°. Since, due to nearly identical refractive indices of the optical waveguide and of the coating, the light can penetrate the interface between the optical waveguide and the coating in nearly unhindered manner, i.e., without reflection, but is reflected at the interface of the coating toward the surrounding medium, for example, air because of the markedly different refractive indices, a twice repeated reflection by 90° takes place. The light beam does not exit the measurement set-up but runs back inside the optical waveguide toward the optical receiver. In such an arrangement, the gas-sensitive layer is consequently crossed by a light beam on four paths, respectively, as a result of which changes in the absorption properties due to a detected gas has a greater effect on the signal registered by the optical receiver than in the case that a gas-sensitive layer is penetrated only once or twice. Apart from a structural simplification due to only one optical waveguide, it is possible for such arrangements to be miniaturized particularly well.

In a preferred application, optical sensors of that kind can be used for analyzing and/or monitoring exhaust gases of internal combustion engines, in particular of internal combustion engines of motor vehicles. In this manner, the measured values obtained from the optical sensor and from an evaluation unit arranged downstream can be used for controlling the internal combustion engine, for example, for complying with exact exhaust values and/or for monitoring and controlling a catalytic afterburning in a catalytic converter in the exhaust train of the internal combustion engine. It is also possible to accurately determine the stoichiometric air ratio, the so-called "lambda value", in exhaust gases of internal combustion engines by determining the contents of $O_2$, CO, $CO_2$, HC, and $NO_x$. By using a plurality of such sensors, it is also possible to carry out a so-called "exhaust-optimized" engine management as well as a permanent monitoring of the combustion processes, as a result of which both the fuel consumption of the internal combustion engine and its exhaust behavior as well as its wear behavior can be optimized.

Moreover, the device according to the present invention can be advantageously used for monitoring an air quality, for example, for controlling ventilation dampers in air conditioning systems. Likewise, devices according to the present invention can be advantageously used for ventilation control and air conditioning in interior spaces. Furthermore, optical sensors according to the present invention can be used for monitoring and/or controlling combustion plants, furnaces, or power plants operated with hydrocarbons. A further possible use is, for example, the measurement of $NH_3$-concentrations in cold storage houses and refrigeration plants using ammonia as a cooling agent. Of course, such optical sensors are also suited for smoke and/or fire detectors, the determination of fire-reference gases by individual optical sensors or a combination of a plurality of sensors allowing the detection and alarm times to be strongly reduced compared to known devices, and allowing the safety against false alarms to be significantly increased.

BRIEF DESCRIPTION OF THE DRAWINGS

FIG. 6 shows an alternative measurement set-up having only one optical waveguide;

FIG. 7 shows a top view of FIG. 6;

FIG. 8 shows a further developed measurement set-up having two optical waveguides and two optical transmitters but only one optical receiver;

FIG. 9 shows a possible top view of FIG. 8;

FIG. 10 shows a different possible top view of FIG. 8;

FIG. 13 shows another possible top view of FIG. 6.

DETAILED DESCRIPTION

Figure 1:
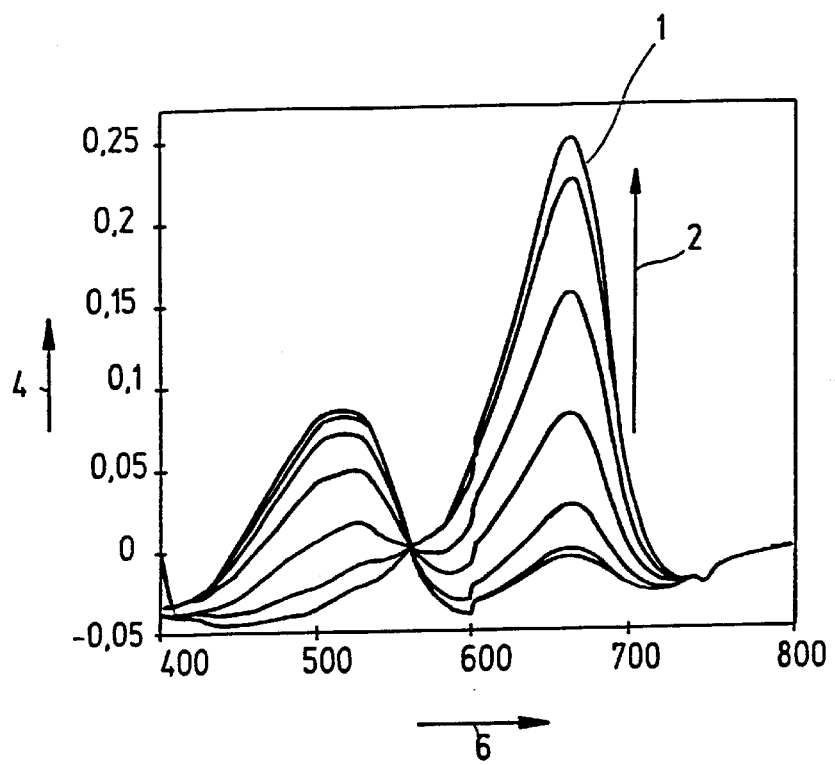
FIG. 1 shows an absorption spectrum of a layer which is sensitive to $NO_x$.

FIG. 1 exemplarily shows, in a diagram, a qualitative connection between the wavelength and the absorption factor of electromagnetic radiation of a gas-sensitive layer at different concentrations of a gas mixture which comes into contact with the gas-sensitive layer. On horizontal axis 6 of the diagram, wavelength λ of the electromagnetic radiation is plotted in nanometers (nm). In the shown exemplary embodiment, the electromagnetic radiation is preferably light within a range which is visible to the human eye. On vertical axis 4, a relative absorption value is plotted which would assume a value of 1.0 in the case of total absorption. In the exemplary embodiment, the gas-sensitive layer is a layer which is sensitive to NO and/or $NO_x$, i.e., which reacts physically and/or chemically with this gas. A set of curves 1 is plotted for different concentrations of NO. It is discernible that, within a certain light wavelength range, in the shown example for example around approximately 670 nm, the absorption of light exhibits a distinct maximum when a specific NO-concentration is present. Set of curves 1 includes a plurality of curves whose respective local maximums, at a constant wavelength, increase with an increasing NO-concentration. In the case of a stronger NO-concentration of the gas mixture interacting with the gas-sensitive layer, transmitting light is absorbed more strongly. This increase is indicated by an arrow 2 perpendicularly directed upward. In the case of the used gas-sensitive layers, a sensor effect, i.e., the changes in absorption or transmission, can generally be detected in relatively narrow wavelength ranges. Suitable as carriers used in the gas-sensitive layer are preferably certain polymers which are chemically substantially inherent so that it is guaranteed that only an indicator substance applied thereto or intercalated therein can interact with the gas and/or gas mixture in question. The gas-sensitive layer can be applied, for example, to a carrier chip. Using this measuring method, moreover, it is possible for a plurality of optical receivers to be provided in each case with different gas-sensitive layers, thus picturing combined optical sensors which respond to a plurality of different gases. For the known indicator substances, the lowest gas concentrations for $NO_x$ that have been detectable hitherto lie in the range of a few ppb.

Figure 2:
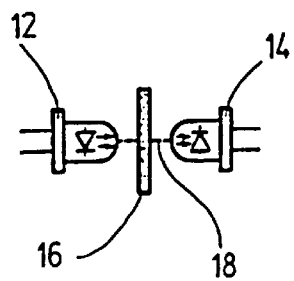
FIG. 2 shows a measurement set-up having a gas-sensitive layer between an optical transmitter and an optical receiver.

FIG. 2 shows a basic measurement set-up for an optical sensor, composed of a source for electromagnetic radiation as optical transmitter 12, in this case a light-emitting diode, and of a detector for electromagnetic radiation as optical receiver 14, for example, a photodiode. Using such components, small, compact and inexpensive optical sensors are picturable, which, in addition, make do with very little energy. It is possible to use optical transmitters 12 and receivers 14 which function with infrared or ultraviolet light, or which function with light in the visible wavelength range. The matching between the wavelength of the light emitted by optical transmitter 12 and the absorbed wavelength of a gas-sensitive layer 16 described in the following is decisive for the functioning of the measurement set-up. A gas-sensitive layer 16 which is permeable to the radiation of optical transmitter 12 and which is composed, for example, of a carrier of polymeric material provided with a specific indicator substance, is located between optical transmitter 12 and optical receiver 14 which is mounted in direct beam path 18 thereof at a certain distance. Gas-sensitive layer 16 is applied to a carrier chip. This gas-sensitive layer 16 which is permeable to the light emitted by optical transmitter 12 can be located exactly in the middle between optical transmitter 12 and optical receiver 14 but can likewise be arranged at any position between optical transmitter 12 and optical receiver 14 provided it is located in beam path 18. In response to an interaction with certain gases, gas-sensitive layer 16 can partially absorb a light of a specific wavelength emitted by optical transmitter 12.

Gas-sensitive layer 16 contains an indicator substance that is sensitive to a specific gas and is calibrated prior to installation by previous calibration measurements. As soon as the gas to be detected enters the region between optical transmitter 12 and optical receiver 14, the indicator substance contained in gas-sensitive layer 16 changes its absorption for specific wavelength ranges of the incident and penetrating electromagnetic radiation. Since this wavelength corresponds to a local absorption maximum of the indicator substance, optical receiver 14 arranged in beam path 18 downstream of gas-sensitive layer 16 registers (senses) a changed transmission. The height of the absorption maximum is proportional to the concentration of the gas. This height of the absorption maximum can be ascertained by an evaluation (not shown here) and can be connected, for example, to a transducer.

Figure 3:
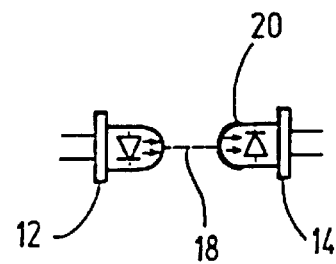
FIG. 3 shows a measurement set-up having a gas-sensitive layer on an optical receiver.

FIG. 3 shows an alternative measurement set-up where a gas-sensitive layer 20 is directly applied to optical receiver 14, in the shown exemplary embodiment a photosensitive photodiode. Identical parts as in FIG. 2 are provided with identical reference symbols and are not explained again. Such a measurement set-up has the advantage of allowing very compact smoke or combustion-gas detectors to be pictured with it.

For detecting different gaseous combustion products, it is possible for a plurality of optical receivers 14 to have layers 20 which are sensitive to different gases, respectively. These optical receivers can all be arranged in beam path 18 of optical transmitter 12 at a certain distance therefrom and, in this manner, are capable of delivering different characteristic absorption signals for different combustion gases to an evaluation unit which is not shown here. However, it is likewise possible for a gas-sensitive layer to be applied to optical transmitter 12.

Figure 4:
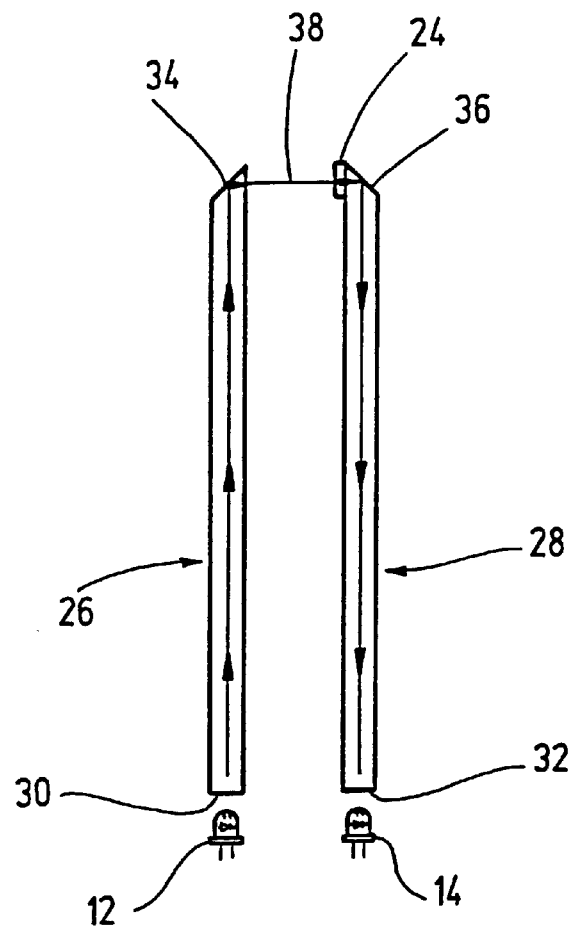
FIG. 4 shows a measurement set-up having optical waveguides between optical transmitter and optical receiver.

FIG. 4 shows a design according to the present invention using optical waveguides arranged in the beam path between optical transmitter 12 and optical receiver 14. Identical parts as in the previous figures are provided with identical reference symbols and are not explained again. In some applications, it is desirable for the gas-sensitive layer to be spatially separated from the optical transmitters and receivers such as in the case of fire detectors or in the case of sensors which are intended to interact with very hot gases. The two semiconductor components can be mounted as surface-mounted devices on a wafer in a housing (not shown here), whereas the gas-sensitive layer can be attached at a location which is accessible to the gas to be detected more easily, i.e., outside the housing. According to the present invention, provision is made for using optical waveguides for optically coupling the gas-sensitive layer to the optical transmitter and receiver. In this context, the light emitted by optical transmitter 12 is coupled into an optical waveguide 26 perpendicularly at a straight end face 30, the optical waveguide having a beveled end face 34 at its other end. Because of this, the coupled-in light is reflected at this end face 34, and, in the case of an angle of end face 34 of 45° to the longitudinal direction of optical waveguide 26, emitted perpendicularly to its longitudinal direction. Light beam 38 which has emerged from optical waveguide 26 can be directed to an optical receiver 14 by an likewise designed further optical waveguide 28. This optical waveguide also has an end face 32 facing optical receiver 14 and being arranged perpendicularly to the longitudinal direction of optical waveguide 28. The opposite end face 36, in turn, has preferably a 45° bevel relative to the longitudinal direction of the optical waveguide, as a result of which light beam 38 impinging on optical waveguide 28 is directed to the optical receiver. A gas-sensitive membrane 24 can be mounted in beam path 38 on each of the two optical waveguides 26, 28 or also between these optical waveguides. In this manner, it is possible for electronics and gas-sensitive layer to be spatially separated.

Figure 5:
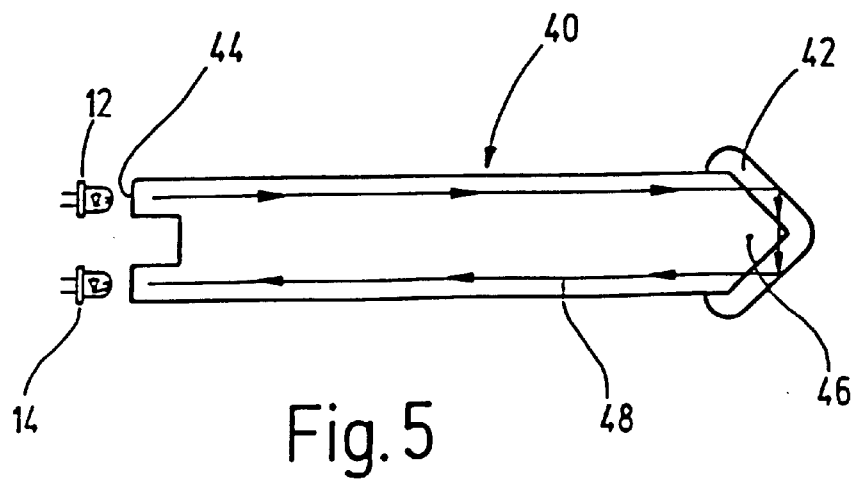
FIG. 5 shows a measurement set-up having only one optical waveguide for optical coupling.

FIG. 5 finally shows a modified measurement set-up using only one optical waveguide. Identical parts as in the previous figures are provided with identical reference symbols and are not explained again. In this measurement set-up, the light which, using optical transmitter 12, is coupled into an end face 44 which is perpendicular to the longitudinal direction of optical waveguide 40, is directed toward a gas-sensitive layer 42 which is applied to conical peak 46 of optical waveguide 40. The interfaces between optical waveguide 40 and gas-sensitive layer 42 are passed through by the light in nearly unhindered manner since both interfaces have nearly identical refractive indices. At the interface between gas-sensitive layer 42 and the ambient air, however, the light is reflected due to the different refractive indices. Corresponding beam path 48 for an angle of 90° of conical peak 46 of optical waveguide 40 is exemplarily plotted in FIG. 5. Beam path 48 experiences a twice repeated deflection by 90°, in each case at the interfaces between air and gas-sensitive layer 42, before the beam path finally runs back, deflected by 180°, to end face 44 and to optical receiver 14 again. In this context, optical receiver 14 and optical transmitter 12 are arranged immediately side by side in a manner that they are parallel to one another. Because the light passes through gas-sensitive layer 42 four times, changes in absorption of the gas-sensitive layer have a stronger effect on the signal detected by the optical receiver than in the case of arrangements according to FIGS. 2 or 3.

Optical waveguide 40 according to FIG. 6, at the end at which optical transmitter 12 (for example a light-emitting diode LED) and optical receiver 14 (for example a photodiode PD) are located, has a slit 49 to prevent light from crossing directly from transmitter 12 to receiver 14. Optical waveguide 40, together with receiver 14 and transmitter 12, can be mounted on a printed-circuit board, and the end having layer 42 can protrude from a housing.

FIG. 7 shows a possible cross-section of optical waveguide 40. However, the cross-section can also be rectangular according to FIG. 13; then layer 42 covers a conical surface portion of optical waveguide 40. Other cross-sectional geometries are possible, as well.

Figure 11:
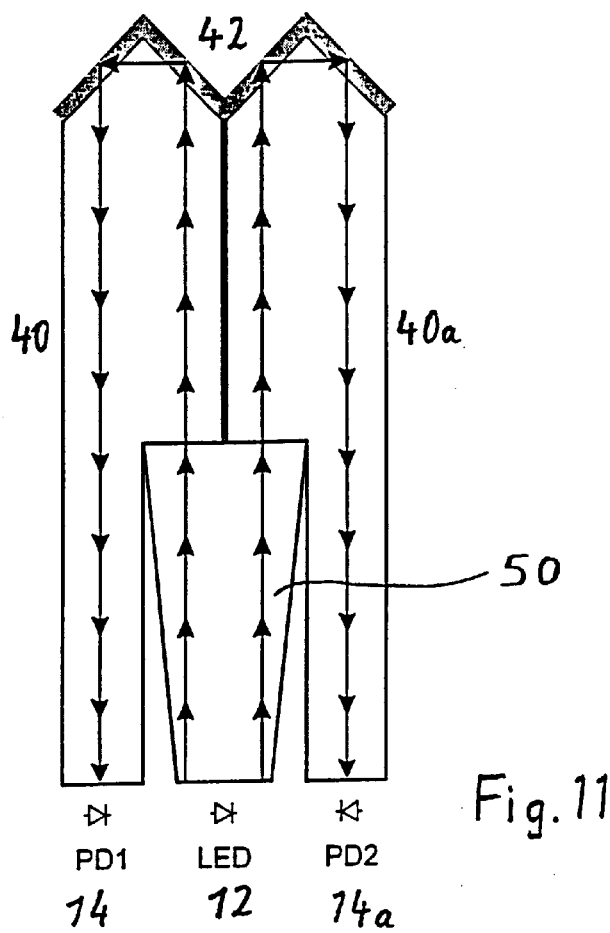
FIG. 11 shows an alternative to FIG. 8.

It is also possible to combine a plurality of optical waveguides 40, 40*a*; either, according to FIG. 8, optical receiver 14 or, according to FIG. 11, optical transmitter 12 being centrally used for a plurality of or for all optical waveguides 40, 40*a*. In this arrangement, it is possible for a plurality of gases to be monitored or for one optical waveguide, if uncoated, to be used as a reference.

Figure 12:
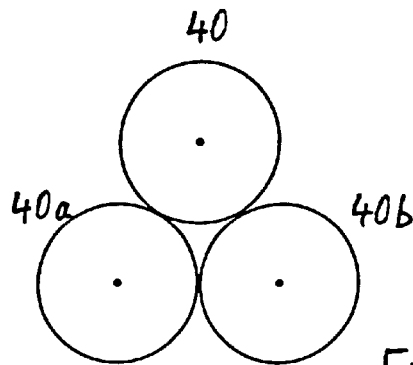
FIG. 12 shows alternative arrangements to FIGS. 7, 9, 10.

FIGS. 9 and 10 show two possible cross-sections of FIG. 8, whereas FIG. 12 shows a cross-section of an arrangement having three optical waveguides 40, 40*a*, 40*b*, for which no view is represented. Located between an insert 50 in FIG. 8 and optical waveguides 40 and 40*a*, respectively, is in each case a slit similar to the slit in FIG. 6.

What is claimed is:

1. An optical sensor for determining at least one of a physical parameter and a chemical parameter of a gas sample, comprising:
   at least one optical transmitter;
   at least one optical receiver;
   an evaluation unit arranged downstream of the receiver; and
   a gas-sensitive element which is arranged in a beam path between the transmitter and the receiver and is exposable to the gas sample, and which changes at least one of a absorption index and a refractive index for electromagnetic radiation of a specific wavelength in a reversible manner in response to a change in parameters of the gas sample, the gas-sensitive element including an indicator substance in a polymer matrix, the transmitter and the receiver being coupled to the gas-sensitive element via at least one optical waveguide, wherein:
   the optical transmitter, the optical receiver, and the gas-sensitive element are matched to a wavelength range,
   the receiver includes a photodiode,
   the gas-sensitive element includes a gas-sensitive layer that changes at least one of the absorption index and the refractive index for electromagnetic radiation in response to contact with a gas or gas mixture,
   the at least one optical waveguide, at an end thereof facing away from the receiver and the transmitter, is chamfered and provided with the gas-sensitive layer, and
   the end of the at least one optical waveguide facing away from the receiver and the transmitter includes a peak having a peak angle of 90°.

2. The sensor of claim 1, wherein the gas-sensitive layer is designed in such a manner that it exhibits a local absorption maximum for electromagnetic radiation in response to an interaction with the gas or gas mixture, the position of the absorption maximum for the gas or gas mixture lying at different wavelengths, and the magnitude of the absorption maximum being correlated with the concentration of the interacting gas or gas mixture.

3. The sensor of claim 2, wherein the transmitter and the receiver are spatially separated from the gas-sensitive layer.

4. The sensor of claim 3, wherein the transmitter and the receiver are spatially and/or structurally combined.

5. The sensor of claim 1, wherein the transmitter and the receiver are integrated on a shared component.

6. The sensor of claim 1, wherein the optical waveguide at its end which is coupled to the gas-sensitive element is chamfered to 45° on its side facing away from the gas-sensitive element.

7. The sensor of claim 1, wherein two optical waveguides at their ends are coupled to the gas-sensitive layer, and wherein each are chamfered to 45° on their sides facing away from the gas-sensitive layer.

8. The sensor of claim 1, wherein the at least one optical waveguide includes a plurality of optical waveguides connected to the transmitter and to the receiver, the plurality of optical waveguides being designed in such a manner that they deflect the electromagnetic radiation coming from the transmitter by 90° into the gas-sensitive layer, and then again by 90° into the receiver.

9. The sensor of claim 1, wherein the transmitter and the receiver are coupled to the gas-sensitive layer via a shared optical waveguide.

10. The sensor of claim 1, wherein the peak is wedge-shaped.

11. The sensor of claim 1, wherein the peak is completely encircled by the gas-sensitive layer.

12. The sensor of claim 1, wherein the peak is conical.

13. The sensor of claim 12, wherein the optical waveguide, at its end facing the transmitter and the receiver, has a planar surface, which is arranged perpendicularly to the longitudinal direction of the optical waveguide.

14. The sensor of claim 1, wherein the optical waveguide connected to the transmitter and the receiver has a longitudinal slit for optical isolation.

15. The sensor of claim 1, wherein the sensor has at least two optical waveguides having an equal number of transmitters, and in that it has only one shared receiver.

16. The sensor of claim 15, wherein one optical waveguide is uncoated and is used as a reference.

17. The sensor of claim 1, wherein the sensor has at least two optical waveguides having an equal number of receivers, and in that it has only one shared transmitter.

18. The sensor of claim 17, wherein one optical waveguide is uncoated and is used as a reference.

19. The sensor of claim 1, wherein the sensor is used for analyzing exhaust gases of an internal combustion engine.

20. The sensor of claim 19, wherein analyzed values obtained from the evaluation unit are used for influencing the control of the internal combustion engine.

21. The sensor of claim 1, wherein the sensor is used for analyzing exhaust gases of an internal combustion engine of a motor vehicle.

22. The sensor of claim 21, wherein analyzed values obtained from the evaluation unit are used for influencing the control of the internal combustion engine.

23. The sensor of claim 1, wherein the sensor is used for monitoring an air quality in interior spaces.

24. The sensor of claim 23, wherein monitored values are used for controlling devices for ventilation and air conditioning control in the interior spaces.

25. The sensor of claim 1, wherein the sensor is used for monitoring and controlling combustion plants and furnaces operated with hydrocarbons.

26. The sensor of claim 1, wherein the sensor is used to detect smoke.

* * * * *

UNITED STATES PATENT AND TRADEMARK OFFICE
CERTIFICATE OF CORRECTION

PATENT NO. : 6,605,804 B1
DATED : August 12, 2003
INVENTOR(S) : Muller-Fiedler et al.

It is certified that error appears in the above-identified patent and that said Letters Patent is hereby corrected as shown below:

<u>Title page,</u>
Item [57], ABSTRACT,
Lines 14-16, delete "Provision is made for the transmitter (12) and for the receiver (14) to be coupled to the sensitive element via at least one optical waveguide (26, 28)."

Signed and Sealed this

Thirteenth Day of July, 2004

JON W. DUDAS
*Acting Director of the United States Patent and Trademark Office*